(12) United States Patent
Kato (10) Patent No.: US 6,737,640 B2
(45) Date of Patent: May 18, 2004

(54) ELECTROSPRAY IONIZATION MASS ANALYSIS APPARATUS AND METHOD THEREOF

(75) Inventor: Yoshiaki Kato, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 10/221,845
(22) PCT Filed: Mar. 31, 2002
(86) PCT No.: PCT/JP02/00808
§ 371 (c)(1), (2), (4) Date: Sep. 16, 2002
(87) PCT Pub. No.: WO03/065405
PCT Pub. Date: Aug. 7, 2003

(65) Prior Publication Data
US 2003/0183757 A1 Oct. 2, 2003

(51) Int. Cl.$^7$ ................................. H01J 27/00
(52) U.S. Cl. ............... 250/281; 250/288; 250/292; 204/180.1; 436/173
(58) Field of Search ............... 250/281, 288, 250/292, 287, 288 R, 288 A; 204/180.1, 183.3, 299 R; 436/173

(56) References Cited

U.S. PATENT DOCUMENTS

| 4,842,701 A | * | 6/1989 | Smith et al. ............. 204/451 |
| 4,861,988 A | | 8/1989 | Henion et al. |
| 5,504,329 A | | 4/1996 | Mann et al. |
| 5,811,800 A | * | 9/1998 | Franzen et al. .......... 250/288 |

FOREIGN PATENT DOCUMENTS

| EP | 565027 A1 | 10/1993 |
| JP | 6-50940 | 2/1994 |
| JP | 6-310088 | 11/1994 |
| JP | 9-180673 | 7/1997 |
| JP | 10-132787 | 5/1998 |
| JP | 2000-340170 | 12/2000 |
| JP | 2001-307675 | 11/2001 |

OTHER PUBLICATIONS

Fujimaki et al "Electrospray Ion Source". Pub No. US 2002/0117629 A1. pub date. Aug. 29, 2002.*

* cited by examiner

Primary Examiner—John R. Lee
Assistant Examiner—Zia R. Hashmi
(74) Attorney, Agent, or Firm—Dickstein Shapiro Morin & Oshinsky LLP (57) ABSTRACT

The object of the present invention is to provide an electrospray ionization mass analysis apparatus and the method thereof provided with an ESI ion source that can be directly coupled to a micro LC.

The present invention provides an electrospray ionization mass analysis apparatus characterized in that a sample solution is led into a capillary tube, and high voltage is applied to the tip of this capillary tube, thereby allowing a spray ion flow of the aforementioned solution to be generated by an electrospray ion source provided therein. The ion flow generated by this ion source is led to an ion storage type spectrometer disposed in an vacuum chamber where it is subjected to mass sweeping, and the swept ion is detected by a detector so that a mass spectrum is obtained. This electrospray ionization mass analysis apparatus is further characterized by comprising a high voltage DC power source for application of the aforementioned high voltage formed by AC voltage superimposed on the DC voltage, and a AC power source.

This invention ensures stable and highly sensitive ESI ionization to be performed at a flow rate ranging from several 10 $\mu$L/min to several $\mu$L/min.

15 Claims, 6 Drawing Sheets

ELECTROSPRAY IONIZATION MASS ANALYSIS APPARATUS AND METHOD THEREOF

FIELD OF THE INVENTION

The present invention relates to a new electrospray ionization mass analysis apparatus and method thereof, wherein a sample solution is led to an electrospray ion (ESI) source and is ionized therein, and the ion generated therein is fed to an ion storage type mass spectrometer arranged in a highly vacuum space, where the ion is subjected to mass analysis.

BACKGROUND OF THE INVENTION

In recent years there has been a remarkable growth in biological researches over diversified fields. Especially, protein, peptide and DNA play an extremely important role in the living body, and have been the objects of study by a great number of research workers.

Generally, these organic compounds derived from living organism occur in a very small amount in a complicated matrix. There has been a growing demand for extract a very small amount of these biological organic compounds from the living body and analyzing them using a mass spectrometer directly coupled with liquid chromatograph LC/MS apparatus) with a high degree of sensitivity. The LC/MS apparatus is an apparatus for separate a mixture with a liquid chromatograph (LC) and providing qualitative and quantitative analysis using a—mass spectrometer (MS) with a high degree of sensitivity. Electrospray ionization (ESI) is typical ionization means used in the LC/MS. The ESI is an ionization technique used under atmospheric pressure and is known as providing soft and highly sensitive ionization. For this reason, this method has come to be used very often for biological analysis.

To ensure stable and highly sensitive measurement of a very small amount of components using the aforementioned ESI, some parameters must be optimized. One of these parameters is the flow rate for supply of the solution to the ESI ion source. To achieve highly sensitive measurement, the flow rate of the solution flowing through the ESI capillary tube must be kept within a certain range. In ESI, the optimum flow rate is said to lie in the range from 10 nL/min ($10^{-8}$ L/min) to several 1 $\mu$L/min ($10^{-6}$ L/min). If a solution is fed into the ESI capillary tube at a flow rate higher or lower than this level, the ESI will become unstable and anticipated highly sensitive measurement will not be achieved.

The flow rate of a conventional LC often used for analysis of a mixture is in the range from several mL/min (several $10^{-3}$ L/min) to several 100 $\mu$L/min (several $10^{-4}$ L/min). The flow rate of the semimicro LC is in the range from 100 $\mu$L/min (several $10^{-4}$ L/min) to several 10 $\mu$L/min (several $10^{-5}$ L/min). Since there is a big difference between the flow rate of the conventional LC and semimicro LC and the optimum ESI flow rate, both type of chromatography have been unable to be directly coupled with the ESI without solution being split. Needless to say, the splitting of solution will cause deterioration of sensitivity in measurement.

Figure 12:
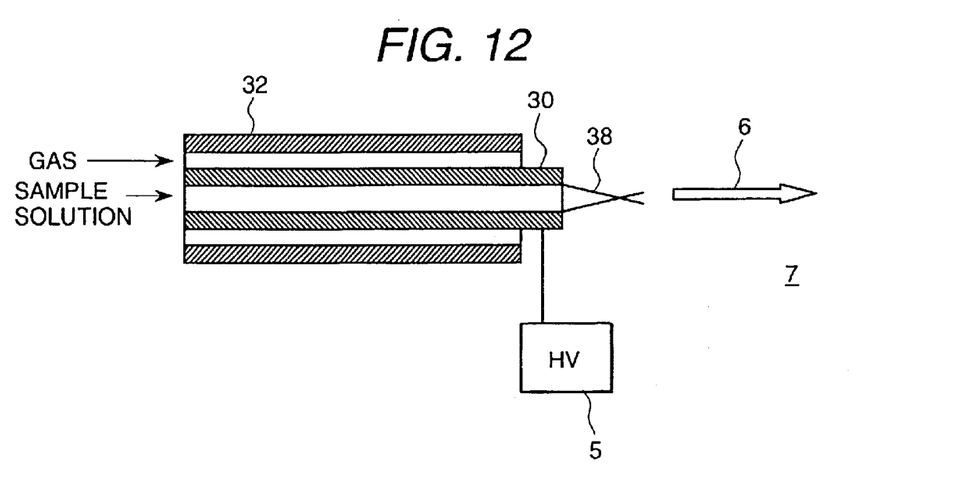
FIG. 12 is a cross section view representing a prior art electrospray probe.

U.S. Pat. No. 4,861,988 discloses the art for improving the ESI to ensure that the aforementioned ESI can be applied to the conventional LC and semimicro LC of high flow rate. According to this art, the spray probe is improved to allow a stable spraying of a large volume of solution. As shown in FIG. 12, the ESI probe consists of two capillary tubes 30 and 32 having different outer diameters. The first capillary tube 30 having a smaller diameter is inserted into the second capillary tube 32 having a larger inner diameter. This configuration provides a coaxial ESI probe. A high voltage of 3 to 4 kV is supplied from the DC high voltage power supply 5 and is applied to the first capillary tube 30. Sample solution is led into the first capillary tube. Nitrogen gas is fed to the space between the first and second. Sample solution is released into the atmosphere as minute charged droplet 6 by the mechanical force and action of electric field. The charged droplet is further pulverized by mechanical crushing due to the flow of gas and evaporation of solution. Ion is released into the atmosphere in the final stage. The generated ion is introduced into a high-vacuum mass spectrometer.

This method has brought about a drastic increase in the flow rate to be introduced into the ESI probe. The increase is from 1 mL/min ($10^{-3}$ L/min) to 100 $\mu$L/min ($10^{-4}$ L/min). This is just applicable to the flow rate of the conventional LC (several mL/min to several 100 $\mu$L/min) and semimicro LC (several 100 $\mu$L/min to several 10 $\mu$L/min). This method has come to be called "Ion Spray" or "Pneumatic Assisted Electrospray".

U.S. Pat. No. 5,504,329 discloses another art of improving the ESI permitting measurement of still further minute components with high sensitivity. The art disclosed therein was later called Nanospray technique. After the tip of an extra-fine capillary tube made of glass having an outer diameter of about 0.2 mm and inner diameter of about 0.03 mm has been elongated by a burner or sharpened by etching, the nozzle tip is gold plated. The D.C. voltage of about 1 kV supplied from the high voltage source is applied to the tip of the nozzle. The flow rate of a sample solution from a nanospray device ranges from is several nL/min (several $10^{-9}$ L/min) to 10 nL/min (several $10^{-8}$ L/min). Measurement for more than one hour was enabled by only the sample sucked into the nanospray spray capillary tube. Accordingly, this nanospray technique has come to be used in combination with extra-low flow rate chromatography in CE (Capillary Electrophoresis); further, it has come to be used for extremely highly sensitive measurement of isolated components. The nanospray technique has enabled ESI measurement in the range of flow rate below 10 nL/min.

Table 1 shows the ESI art, improved ionization arts, optimum flow rate and compatible chromatography:

TABLE 1

| No | Ionization | Optimum flow rate | Compatible chromatography |
| --- | --- | --- | --- |
| 1 | Ion Spray | 1 mL/min to 100 $\mu$L/min | Conventional LC, semimicro LC |
| 2 | ? | Several 10 $\mu$L/min to 1 $\mu$L/min | Micro LC |
| 3 | ESI | 1 $\mu$L/min to 10 nL/min | Capillary LC |
| 4 | Nanospray | 1 nL/min to 10 nL/min | Capillary electrophoresis |

The advent of Ion Spray, ESI and Nanospray has enabled selection of an ion source suited to each one of various types of chromatography. However, as shown in Table 1, there is no ESI ion source that is best suited to the micro LC from 10 $\mu$L/min to 1 $\mu$L/min. For this reason, the researchers have to use the ESI or Ion Spray for the micro LC, based on the understanding that the sensitivity and stability are not satisfactory.

For the micro LC, the flow rate of mobile phase is from 10 $\mu$L/min to 1 $\mu$L/min and the required amount of sample solution can also be reduced to the level as small as nL($10^{-9}$ L/min). So its range of application is rapidly expanding to cover the field of analyzing the biological component.

Needless to say, there has been a growing demand for ionization technique optimum to this field.

DISCLOSURE OF THE INVENTION

The object of the present invention is to provide an electrospray ionization mass analysis apparatus and the method thereof provided with an ESI ion source that can be directly coupled to the micro LC.

The present invention provides an electrospray ionization mass analysis apparatus wherein:

a sample solution is led into a capillary tube under atmospheric pressure, voltage or electric field is applied to the tip of this capillary tube, thereby allowing an ion to be generated by an electrospray ion source provided therein, and generated ion is led to and stored in an ion storage type spectrometer disposed in a vacuum chamber so that a mass spectrum is obtained by subsequent mass sweeping. This electrospray ionization mass analysis apparatus is characterized in that the voltage formed by AC voltage superimposed on the DC voltage or the electric field formed by AC electric field superimposed on the static electric field is applied to the tip of the aforementioned capillary tube, whereby electrospray ionization is carried out.

The present invention provides an electrospray ionization mass analysis apparatus wherein:

a sample solution is led into a capillary tube; high voltage is applied to the tip of this capillary tube, thereby allowing a spray ion flow of the aforementioned solution to be generated by an electrospray ion source provided therein; and the ion flow generated by this ion source is led to an ion storage type spectrometer disposed in an vacuum chamber where it is subjected to mass sweeping, and the swept ion is detected by a detector so that a mass spectrum is obtained. This electrospray ionization mass analysis apparatus is characterized by comprising a high voltage DC power source for application of the aforementioned high voltage formed by AC voltage superimposed on the DC voltage, and a AC power source.

The present invention provides an electrospray ionization mass analysis apparatus wherein:

a sample solution is separated by a micro liquid chromatograph;

the sample solution separated by the micro liquid chromatograph is led into a capillary tube;

high voltage is applied by a high voltage power source connected between the tip of the capillary tube and a counter electrode having an aperture, thereby allowing a spray ion flow to be generated to flow from the tip of the capillary tube toward the aperture by an electrospray ion source provided therein; and the ion flow generated by this ion source is sequentially led from the aperture to a skimmer cone and ion guide disposed in an vacuum chamber, and then to the ion storage type spectrometer where it is subjected to mass sweeping and the swept ion is detected by a detector so that a mass spectrum is obtained. This electrospray ionization mass analysis apparatus is further characterized in that the aforementioned high voltage power source comprises a high voltage DC power source for application of DC voltage and an AC power supply for application of AC voltage, wherein the voltage is formed by the aforementioned AC voltage superimposed on the aforementioned DC voltage.

The present invention provides an electrospray ionization mass analysis apparatus characterized by one of the following configurations; (1) the aforementioned skimmer cone, ion guide and ion storage type mass spectrometer are each disposed integrally in each vacuum chamber, which is provided with a vacuum pump; (2) an XYZ3 axis positioner for setting the spray ion flow with respect to the aforementioned capillary tube is connected; and (3) the ion storage type mass spectrometer is an ion trap mass spectrometer or an ion cyclotron resonance (ICR) mass spectrometer.

The present invention provides an electrospray ionization mass analysis apparatus wherein:

a sample solution is led into a capillary tube under atmospheric pressure;

high voltage is applied to the tip of this capillary tube, thereby allowing a spray ion flow of the aforementioned solution to be generated; and the generated ion flow is led to an ion storage type spectrometer disposed in an vacuum chamber where it is subjected to mass sweeping, and the swept ion is detected by a detector so that a mass spectrum is obtained. This electrospray ionization mass analysis apparatus is characterized in that the voltage formed by AC voltage superimposed on the DC voltage or the electric field formed by AC electric field superimposed on the static electric field is applied to the tip of the aforementioned capillary tube.

The present invention provides an electrospray ionization mass analysis apparatus wherein:

a sample solution is separated by a micro liquid chromatograph;

the sample solution separated by the micro liquid chromatograph is led into a capillary tube;

high voltage is applied to the tip of the capillary tube, thereby allowing a spray ion flow to be generated to flow from the tip of the capillary tube; and the generated ion flow is sequentially led to a skimmer cone and ion guide disposed in an vacuum chamber, then to the ion storage type spectrometer where it is subjected to mass sweeping, and the swept ion is detected by a detector so that a mass spectrum is obtained. This electrospray ionization mass analysis apparatus is characterized in that the voltage formed by AC voltage superimposed on the DC voltage or the electric field formed by AC electric field superimposed on the static electric field is applied to the tip of the aforementioned capillary tube.

The present invention provides an electrospray ionization mass analysis apparatus characterized by one of the following configurations; the aforementioned DC voltage and AC voltage or the intensity of static electric field and AC electric field can be set and controlled from the outside; when the aforementioned spray ion flow is in the positive ion measurement mode, the polarity of the aforementioned DC voltage or static field is positive; and when the aforementioned spray ion flow is in the negative ion measurement mode, the polarity of the aforementioned DC voltage or static field is negative; the aforementioned AC voltage is 100% or less of the DC voltage, or the AC electric field is 100% or less of the static electric field, preferably, in the range from 10 to 65%, more preferably in the range from 15 to 50%; the frequency of the aforementioned AC voltage or AC electric field is 1 kHz or less, preferably in the range from 31 to 330 Hz, more preferably in the range from 50 to 300 Hz; the flow rate of the solution led into the capillary tube under atmospheric pressure is 50 $\mu$L/min or less, preferably 20 $\mu$L/min or less; and high voltage applied to the tip of the capillary tube is such that the sample solution is formed in a Taylor cone shape at the outlet of the capillary tube.

The present invention according to any one of the aforementioned methods is characterized in that the aforementioned ion storage type spectrometer is an ion trap type spectrometer, and the following steps are incorporated:

(1) Preparatory step wherein the voltage formed by DC voltage superimposed on AC voltage is applied to the capillary tube. Voltage of the same polarity as that of ion is applied to the ion gate electrode arranged on the front stage of the ion trap type spectrometer so that ion will not be led into the ion trap. The main high frequency voltage applied to the ring electrode constituting the ion trap electrode is reset to zero to remove all the ions in the ion trap.

(2) Ion introduction and storage step wherein voltage of the polarity reverse to that of ion is applied to the ion gate electrode so that ion can be led into the ion trap. The main high frequency voltage is applied to the ring electrode so that the ion in a predetermined mass range is led into the ion trap, and ion storage is carried out for a predetermined period of time level out the ion current.

(3) MS/MS step wherein voltage of the same polarity as that of ion is applied to the ion gate electrode to block introduction of the ion. The ion in the aforementioned ion trap is selected and collision dissociation (CID) is carried out. This step can be omitted according to the purpose of each analysis.

(4) Mass spectrum acquisition step wherein the main high frequency voltage applied to the ring voltage is swept and the ions in the ion trap are discharged out of the ion trap sequentially in the order of the mass. Ion current value is detected by a detector and the detected signal is fed to a control data processor, where the mass spectrum is obtained.

Namely, the mass analysis using the ESI according to the present invention is carried out as follows: Voltage of several kilovolts is applied between a metallic capillary having an inner diameter of about 0.1 mm and a counter electrode arranged at some distance (about several tens of mm) away therefrom. When a sample solution is led to the metallic capillary and a high voltage is applied, the liquid in the capillary is dielectrically polarized at the capillary outlet by a high electric field formed on the tip of a metallic capillary. In the positive ionization mode, positive electric charge is induced on the liquid surface, while in the negative ionization mode, negative electric charge is induced on the liquid surface.

As a result, a conical liquid called Taylor cone is pulled out into the atmosphere from the capillary outlet by electric field. If electric field is stronger than the surface tension at the tip of the Taylor cone, electrically charged extremely fine droplets are released into the atmosphere from the tip of the Taylor cone. In conformity to electric field, the generated charged droplets fly in the atmosphere toward a counter electrode to repeat collision with molecules in the atmosphere.

This allows charged droplets to be mechanically crushed, and evaporation of solvent from the droplet surface is promoted so that charged droplets are quickly pulverized. In the final stage, ions in charged droplets are released into the atmosphere. The ion flies in the atmosphere toward a counter electrode and is led into a highly vacuum mass spectrometer through a capillary tube or aperture arranged in the counter electrode where it is subjected to mass analysis.

In the present invention using the micro LC, the flow rate of mobile phase is several tens of 10 $\mu$L/min to 1 $\mu$L/min and the required amount of sample solution to be supplied is as small as nL($10^{-9}$ L/min). Accordingly, its application can be expanded to the field of analysis of biological related components where trace quantities of components are handled.

BEST FORM OF EMBODIMENT OF THE PRESENT INVENTION

Figure 1:
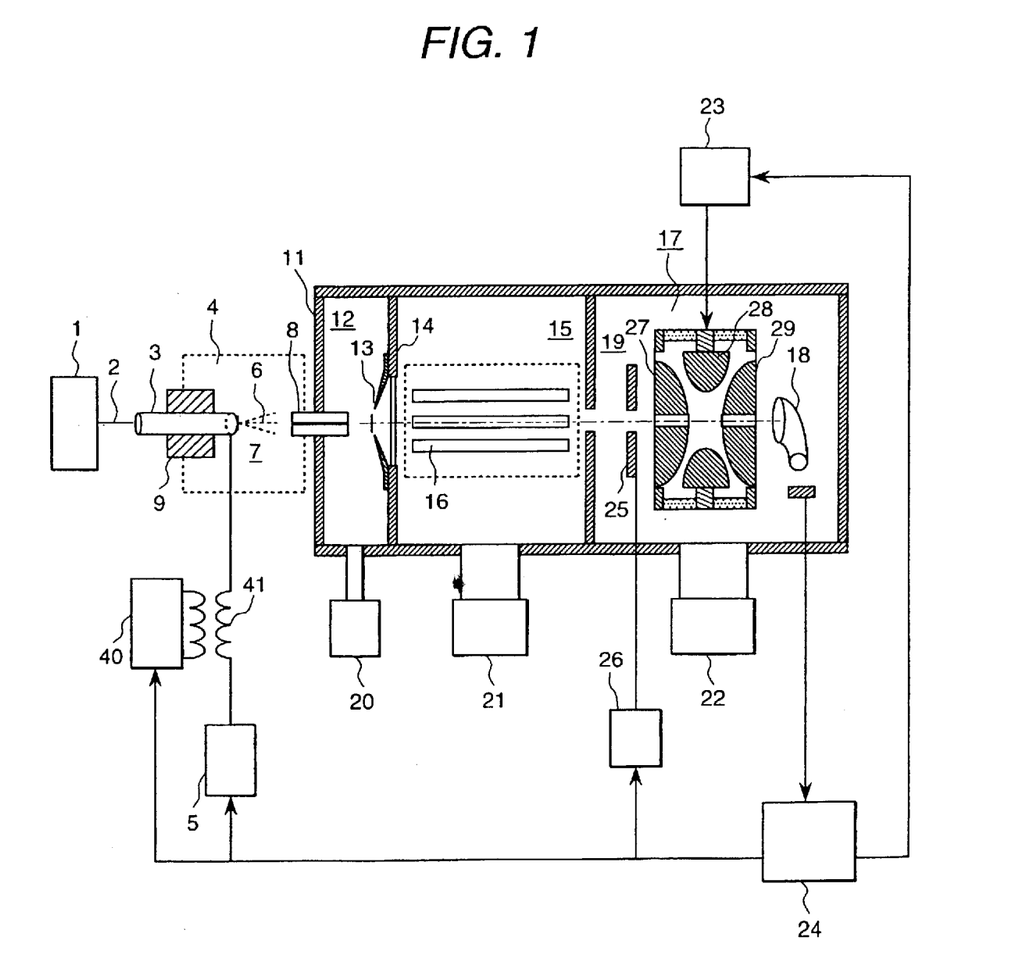
FIG. 1 is an overall configuration drawing of electrospray ionization mass analysis apparatus as an embodiment of the present invention.

FIG. 1 is an overall configuration drawing of electrospray ionization mass analysis apparatus as an embodiment of the present invention. The sample solution separated for each component by the micro LC 1 is sent to the ESI probe 3 of the ESI ion source 4 through a capillary tube 2. The ESI probe 3 is arranged on the XYZ three-axis positioning device 9. The sample solution is fed in a capillary tube 30 constituting the ESI probe 3 to reach the tip of the capillary tube nozzle. DC voltage Vd is applied to the ESI nozzle 31 from a high voltage DC power source 5 through a transformer 41. Further, AC voltage Va is applied to the ESI nozzle 31 from an AC power source 40 through a transformer 41, at the same time. That is, Voltage Va+Vd obtained by the DC voltage superimposed on AC voltage is applied to the ESI nozzle. AC-modulated DC field is created in the vicinity of the ESI nozzle tip 33 by this superimposed voltage.

An ion guide 16 consists of cylindrical electrodes formed by four, six and eight metallic rods arranged on a certain circumference at an equally spaced interval. These rods are wired alternately and high frequency is applied between two electrodes. When the ion is led onto the center axis of this ion guide, the ion is subjected to vibration by high frequency and is brought into collision with gas molecule to be converged on the ion guide axis. Ion can be transferred by this ion guide without being lost.

The capillary tube 8 is a pipe made of stainless steel, other metal or glass. Preferably, it has an inner diameter of 0.4 to 0.3 mm and a length of 10 cm. It is used with a heater arranged around it for heating.

The ion trap mass spectrometer 17 is composed of three electrodes as rotary symmetric elements of hyperbolic curve, and a toroidal ring electrode 28 and two end cap electrodes 27 and 28 sandwiching it are arranged. When main high frequency voltage is applied to the ring electrode 28 from the main high frequency power source 23, a quadrupole electric field is formed in the space formed by these three electrodes. The ion generated by the ESI ion source is fed to the vacuum space to reach the ion trap mass spectrometer 17 through the skimmer and ion guide. The ion is led in an ion trap or is blocked therefrom by an ion gate electrode 25 arranged in front of the ion trap electrode.

When voltage with the same polarity as that of the ion is applied to the ion gate electrode 25, the ion will be blocked, namely, the ion gate is turned off. Conversely when voltage with the polarity reverse to that of the ion is applied, ion is led into the ion trap, namely, the ion gate is turned on.

Ions can be also stored in the ion trap by introducing them for a predetermined time when the main high frequency voitage is applied to the ring electrode 28. This ensures the average mass spectrum to be obtained even if the amount of ions in the ion source fluctuate. The mass spectrum can be obtained by performing MS/MS with the ion gate turned off and sweeping the main high frequency voltage applied to the ring electrode.

In the figure, numeral 1 denotes a micro LC, 2 a capillary tube, 4 a ESI ion source, 6 a spray ion flow, 7 a ion source space, 14 a vacuum partition, 15 a vacuum chamber, and 20, 21 and 22 vacuum pumps.

Figure 2:
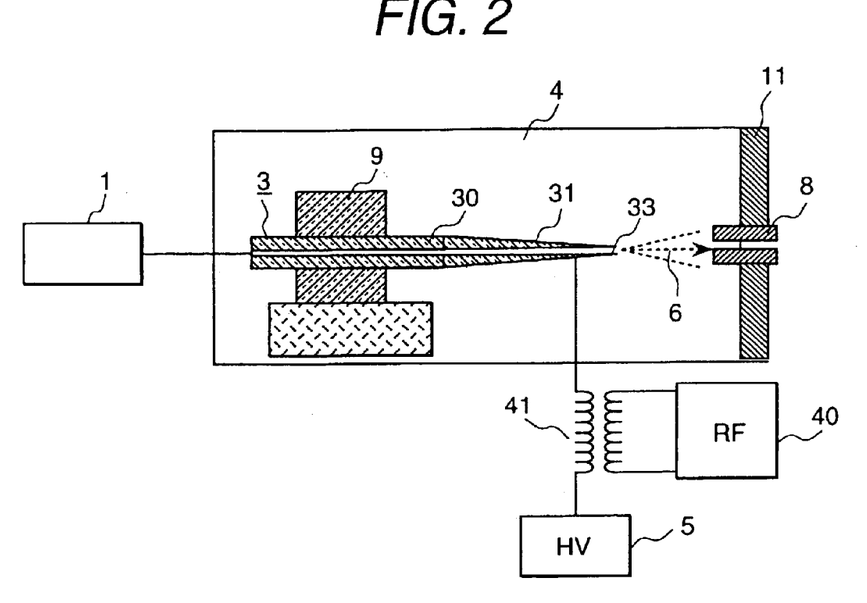
FIG. 2 is an enlarged view of an apparatus for forming the spray ion flow as an embodiment of the present invention.

FIG. 2 is an enlarged view of an apparatus for forming the spray ion flow as an embodiment of the present invention. As shown in FIG. 2, the superimposed AC/DC voltage can be created by coupling the DC power source 5 and AC power source 40 with a transformer 41. It can also be created by using a capacitor instead of a transformer.

Figure 3:
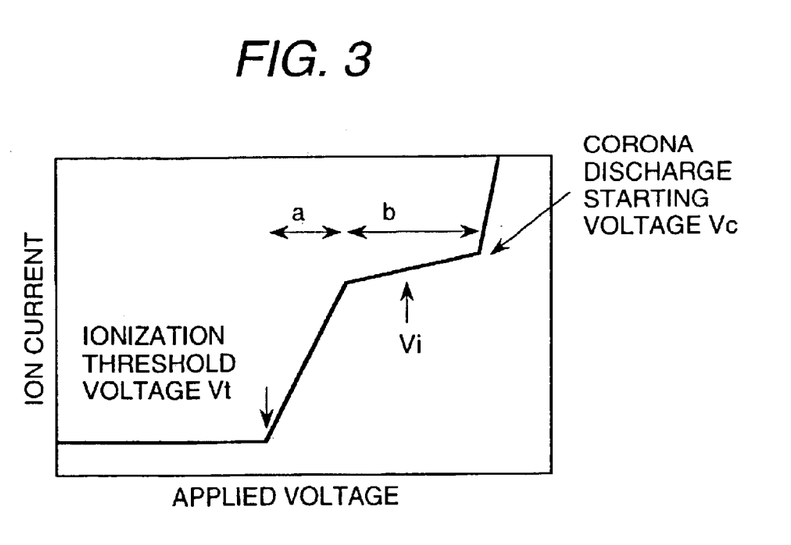
FIG. 3 is a diagram representing the relationship between voltage HV applied to the ESI nozzle and ion current to be generated according to the present invention.

FIG. 3 is a diagram representing the relationship between voltage HV applied to the ESI nozzle and ion current to be generated. As shown in FIG. 3, when the voltage HV applied to the electrospray nozzle is gradually increased, ionization starts at a certain voltage Vt to get ion current. This Vt is called ionization threshold voltage. With the increase of the applied voltage, the ion current to be detected exhibits a rapid increase (for period "a"). After that, increase of the ion current becomes gradual (period "b"). If the applied voltage HV is further increased, ion current exhibits a sudden increase from a certain voltage Vc.

This sudden increase of ion current can be explained as follows: When the applied voltage HV has exceeded Vc, corona discharge starts from the ESI nozzle tip. This corona discharge starts Atmospheric Pressure Chemical Ionization (APCI) resulting in a sudden increase of ion current. APCI is ionization caused by the ion molecular reaction started by electron. Accordingly, this APCI provides an ion species entirely different from that of the ESI. To ensure a stable ESI mass spectrum, it is important to apply voltage Vi to the ESI nozzle for the period equivalent to Period "b". These voltages Vt and Vi greatly depend on the structure of the apparatus and physical and chemical properties of the sample solvent. According to the experiments of the present inventors, the ionization threshold voltage Vt was 1.5 kV.

Figure 4:
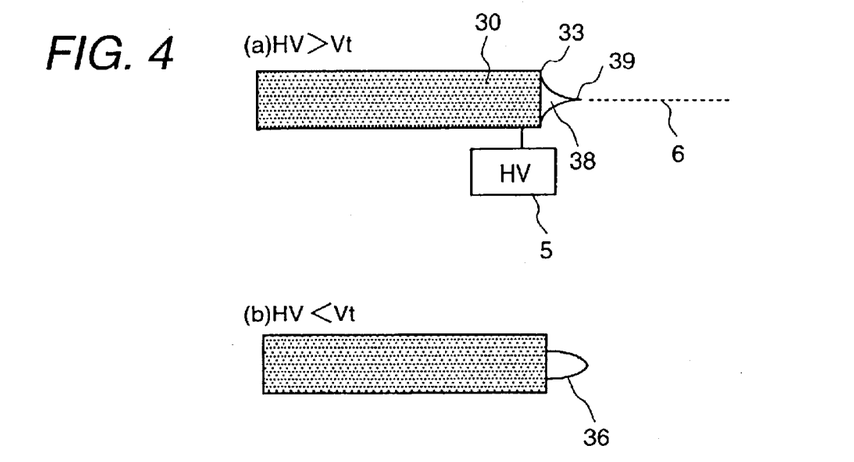
FIG. 4 is a diagram representing the relationship between the applied voltage and form of the spray ion flow according to the present invention.

FIG. 4 is a diagram representing the relationship between the applied voltage and form of the spray ion flow.

As shown in FIG. 4(a), when the applied voltage HV has exceeded the ionization threshold voltage Vt, Taylor Cone 38 is formed on the ESI nozzle tip 33, with the result that the strength of electric field exceeds the surface tension of the solution. Then the electrically charged droplet 6 is released into the atmosphere through the tip 39 of the Tailor Cone 38, and the ESI (electrospray ionization) starts. Conversely, as shown in FIG. 4(b), when the applied voltage HV has reduced below the Vt, the surface tension exceeds the force of electric field and the Taylor Cone fails to maintain the sharp angle so that it is changed to a cone 36 having an obtuse angle. In this state, electrically charged droplets cannot be produced. That is, this is the state where ESI has stopped. While ESI continues, the force of electric field greater than the surface tension must be maintained on the tip of the Taylor Cone. The strength of the electric field is determined by the voltage HV applied between the ESI probe tip and counter electrode and the distance between the ESI probe tip and counter electrode.

Figure 5:
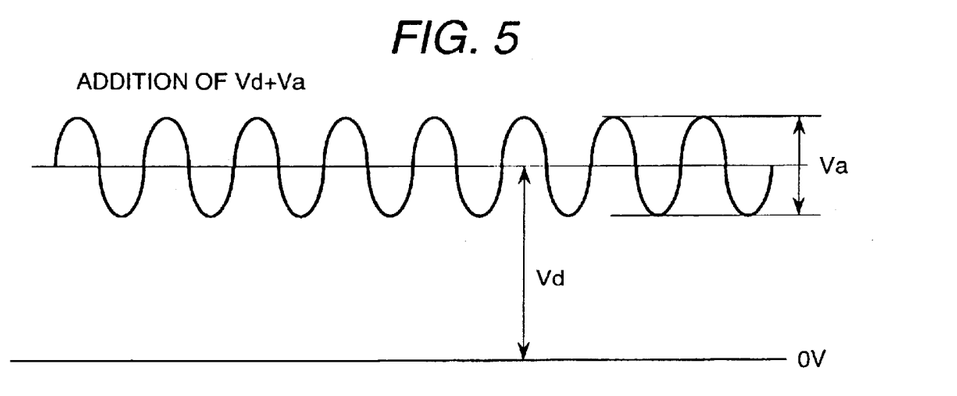
FIG. 5 is a diagram representing the waveform of the voltage obtained by application of AC voltage to the DC voltage according to the present invention.

FIG. 5 is a diagram representing the waveform of the voltage obtained by application of AC voltage to the DC voltage. As shown in FIG. 5, superimposed AC/DC voltages appear in the following four forms, depending on the relationship between AC voltage Va and DC voltage Vd to be applied, and ionization threshold voltage Vt. In the drawing, 36 denotes the solution cone, 37 a sample solution, 39 a Taylor cone tip and 43 the direction of the electric field.

$$Vd - \tfrac{1}{2}(Va) > Vt \tag{1}$$

The strength of the electric field in the vicinity of the ESI nozzle always exceeds the ionization threshold voltage (Vt). Consequently, the charged droplet is always discharged from the tip of the Taylor Cone. The ESI is always continued and ion current value can be obtained at all times. However, the ion current is not constant. It increases or decreases with in synchronism with the AC cycle.

$$Vd = Vt \tag{2}$$

A half cycle of the AC component is $Vd - \tfrac{1}{2}(Va) < Vt$. During this period, the Taylor Cone is not generated, and the ESI stops. The next half cycle occurs and $Vd + \tfrac{1}{2}(Va) > Vt$ so that the Taylor Cone is generated, with ion being generated from the tip thereof. This results in continuation of the ESI.

$$Vd + \tfrac{1}{2}(Va) > Vt \tag{3}$$

Only at the instant when the superimposed voltage has exceeded the ionization threshold value (Vt), ESI is performed. During the time when the superimposed voltage is below the ionization threshold value (Vt), ESI stops and ion current cannot be obtained.

$$Vd + \tfrac{1}{2}(Va) < Vt \tag{4}$$

Since the voltage applied to the ESI nozzle 31 is always below the ionization threshold voltage Vt, ionization is not carried out.

Figure 6:
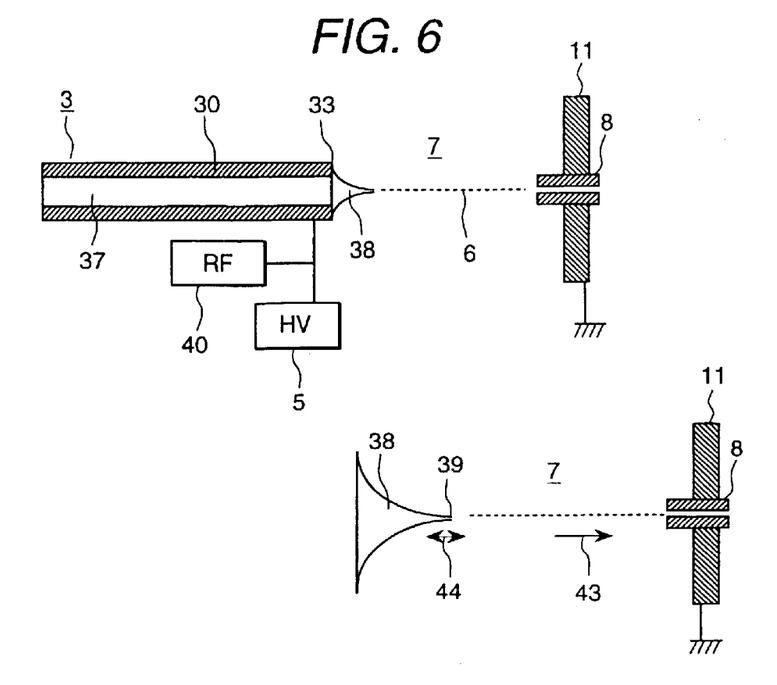
FIG. 6 is a diagram representing the form of the spray ion resulting from application of AC voltage to the DC voltage according to the present invention.

FIG. 6 is a diagram representing the form of the spray ion resulting from application of AC voltage to the DC voltage.

Figure 7:
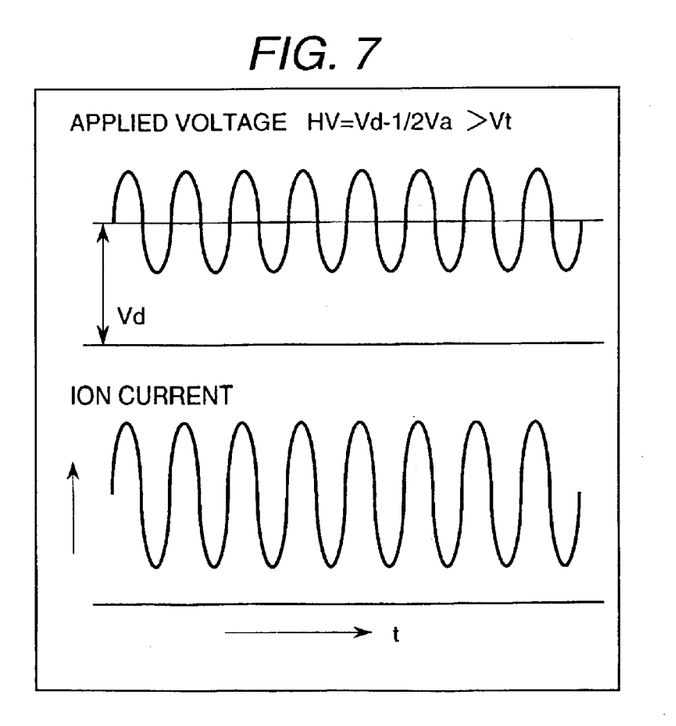
FIG. 7 is a diagram representing the relationship between threshold voltage and ion voltage according to the present invention.

In this invention, the superimposed voltages corresponding to (1) to (3) are applied. In the case (1), the Taylor Cone 38 is stably generated on the tip 33 of the capillary tube 30, as shown in FIG. 6. The charged droplet is always generated from the tip of the Taylor Cone 38. Thus, ion is generated by ESI. However, since the electric field has been subjected to AC modulation, it will undergo the change 44 in the force of electric field. This change 44 in the force gives constant stress and vibration to the Taylor Cone 38. This vibration 44 promotes separation of the charged droplet from the Taylor Cone 38. Since the electric field is AC-modulated, the generated ion current value is constantly subjected to fluctuation, as shown in FIG. 7. The ion current value takes the form of having been AC-modulated. However, the applied voltage HV is not reduced below the ionization threshold voltage Vt, so ion current value does not become zero.

Figure 8:
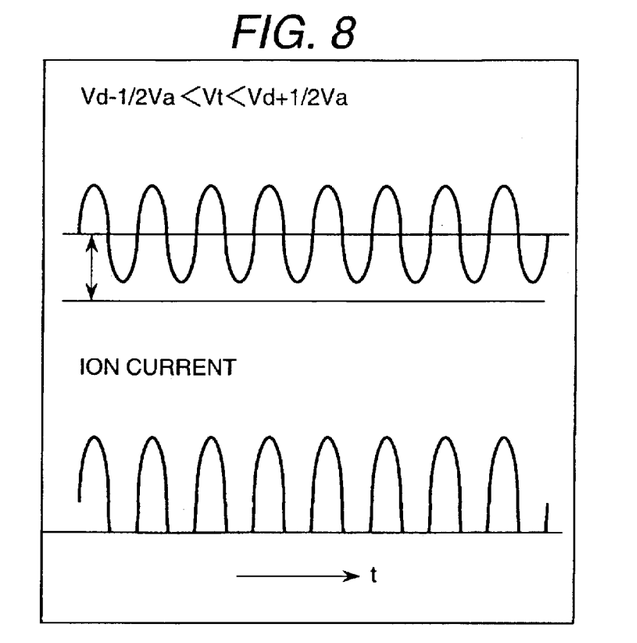
FIG. 8 is a diagram representing the relationship between threshold voltage and ion current according to the present invention.

In the case of (2) and (3), there are a moment when the applied voltage HV has exceeded the ionization threshold value Vt, and a moment when it has fallen below the Vt. When it has exceeded the ionization threshold value Vt, ion is generated, but when it has fallen below the Vt, ion is not generated. For this reason, the generated ion current exhibits a form of intermittent pulses as shown in FIG. 8.

As shown in FIG. 1, the charged droplet generated by the ESI ion source flies in the atmosphere along a electric field, and ions are discharged into the atmosphere. The discharged ions are led into the vacuum chamber 12 through the capillary tube 7 provided on the partition of the vacuum chamber 11. Ions are further fed into the high-vacuum chamber 19 through the skimmer 13 and ion guide 16 disposed in the vacuum chamber 15. Then the ions go to the ion trap mass spectrometer 17 through the ion gate 25. The ion trap mass spectrometer 17 is composed of three electrodes as rotary symmetric elements of hyperbolic form. Two end cap electrodes 27 and 28 are arranged so as to sandwich the toroidal ring electrode 28. Main high frequency voltage is applied to the ring electrode 28 from the main high frequency power source 23, and a quadrupole electric field is formed in the ion trap space. This ensures stable trapping of the ion introduced into the ion trap space. Upon termination of the ion introduction and storage period, voltage with the same polarity as that of the ion is applied to the ion gate 25, which is turned off.

Then the main high frequency voltage supplied from the high frequency power source 23 is swept, and ions are released from the ion trap space sequentially in the order of mass. The signal is sent to a control data processor 24 where the mass spectrum is given.

In the case of superimposed voltage the change of the electric field strength acting on the Taylor Cone results from the amplitude of the applied AC voltage. For this reason, Taylor Cone vibration and amplitude can be controlled by controlling the amplitude of this AC voltage with the control data processor 24 through high voltage DC power source 5 and AC power source 40. AC voltage Va should be adjusted by monitoring the amount of ion, and should be set in such a direction that the ion current value increases. In the same manner, the DC voltage Vd should be adjusted and set in such a way that the ion current value will be maximized. Unlike the mechanical vibration due to an ultrasonic element, the vibration due to the AC electric field of the present invention causes only the tip of the Taylor Cone to be subjected to the fluctuation of force. Mechanical vibration does not influence the ESI capillary tube. Consequently, the relationship between ion current value and AC voltage Va is highly reproducible. It is easy to adjust the AC or DC voltage to obtain the optimum conditions.

The LC/MS measurement is available in two modes; positive ion mode and negative ion mode. In the positive mode, positive ions are generated by the ion source and a positive ion mass spectrum is obtained from the mass spectrometer. In the negative ion mode, a negative ions are generated by the ESI ion source and a negative ion mass spectrum is gained from the mass spectrometer. In the present invention, the DC power source polarity is switched in response to the polarity switching command from the control data processor 24 sent to the high voltage DC power source 5. The polarity of the DC voltage Vd is positive in the positive ion mode, and is negative in the negative ion mode. The superimposed AC voltage may stay unchanged. This allows the ESI polarity to be switched.

Application of this superimposed AC voltage greatly promotes generation of droplets from the Taylor Cone, hence generation of ions. In other words, this makes it possible to substantially increase the flow rate of the solution that can be introduced into the ESI ion source. According to the experiment of the present inventors, there is an increase in the flow rate and the amount of ions by ten times to several tens of times, compared to the case of ESI when independent DC voltage is applied. However, on the other hand, a great change occurs to the amount of generated ion since it is synchronized with the AC cycle, as shown in FIGS. 7 and 8. When the ion current always changes in this manner, correct Mass spectrum cannot be obtained if a quadrupole amplifier (QMS), magnetic field type MS, time-of-flight mass spectrometer (TOF) and other sweep type mass spectrometer if used as the mass spectrometer. This is because sweeping for mass spectrum acquisition does not synchronize with the change in the ion current value. However, there is a mass spectrometer that ensures a correct mass spectrum even if the ion current value changes. Such a spectrometer is an ion storage type mass spectrometer.

The ion storage type mass spectrometer ensures ion introduction and storage, MS/MS treatment, mass spectrum sweeping to be carried out with the lapse of time on a time division basis. The ion trap mass spectrometer is an ion storage type mass spectrometer, and other well-known mass spectrometers include an ion cyclotron resonance (ICR) mass spectrometer (also called FT/MS). Especially since ion introduction and storage and mass spectrum are independently treated and handled, mass spectrum will not be affected at all if the ion current value can be changed with excellent reproducibility during the ion introduction and storage period.

Figure 9:
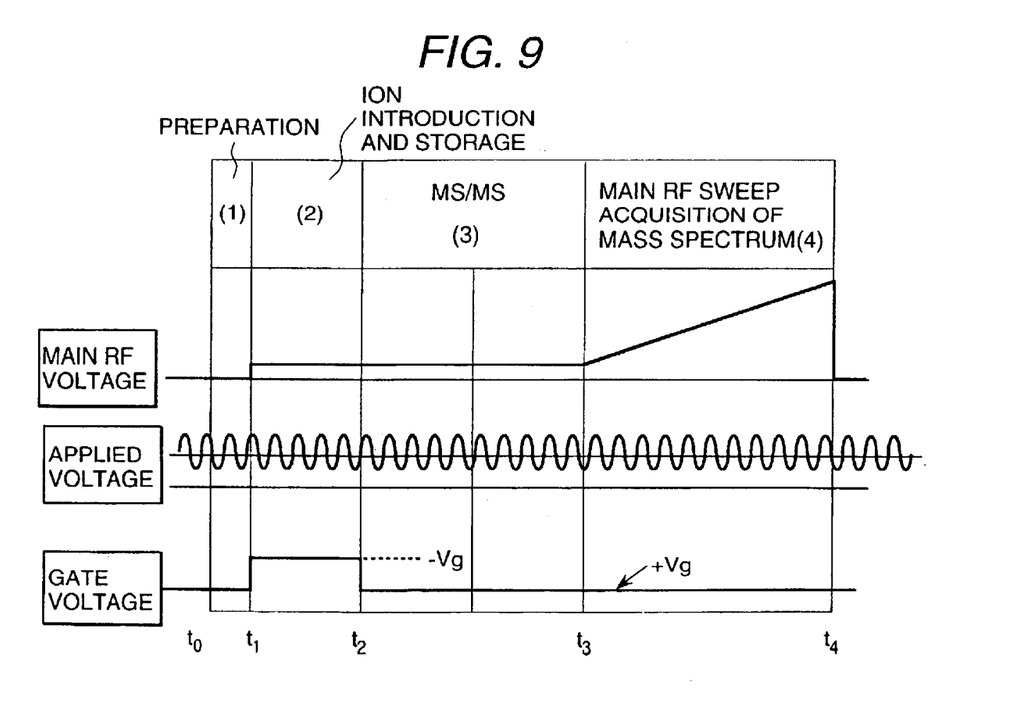
FIG. 9 is a diagram representing the operation sequence of an ion trap spectrometer.

FIG. 9 is a diagram representing the operation sequence of an ion trap spectrometer;

(1) Preparatory period ($t_0$ to $t_1$); The high voltage HV formed by DC voltage superimposed on AC voltage is applied to the ESI nozzle. This will cause the ESI to be started. Voltage of the same polarity as that of ion is applied to the ion gate electrode 25 to block the entry of ion. The main high frequency voltage applied to the ring electrode 28 is reset to zero to remove all the ions in the ion trap.

(2) Ion introduction and storage period ($t_1$ to $t_2$); A predetermined main high frequency voltage is applied to the ring electrode 28 of the ion trap from the main high frequency power source 23. The ion in a predetermined mass range is trapped into the ion trap, and voltage of the polarity reverse to that of ion is applied to the ion gate electrode 25 from the ion gate electrode 26. The ion generated in the ESI is led and stored in the ion trap. The AC-modulated ion is also averaged during this ion introduction and storage period.

(3) MS/MS period ($t_2$ to $t_3$); Voltage of the same polarity as that of ion is applied to the ion gate electrode 25 to turn off the ion gate and to block introduction of the ion. The ion in the d ion trap is selected and collision induced dissociation (CID) is carried out. This provides new information. This step can be omitted according to the field of application.

(4) Mass spectrum acquisition period ($t_3$ to $t_4$); The main high frequency voltage applied to the ring electrode 28 from the main high frequency power source 23 is swept. Then the ion in the ion trap is discharged out of the ion trap sequentially in the order of the mass. Ion current value is detected by a detector 18. This signal is fed to a control data processor 24, where the mass spectrum is acquired.

A mass spectrum is repeatedly obtained by repetition of the above steps (1) to (4). The components sent from the chromatograph are ionized by ESI and mass spectrum is obtained.

Figure 10:
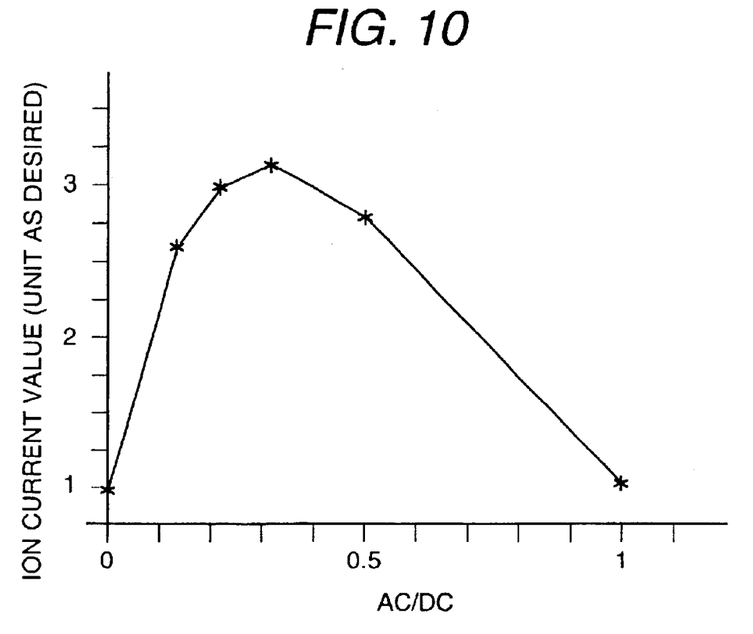
FIG. 10 is a diagram representing the relationship between ion current (unit as desired) and the ratio of DC voltage Vd to AC voltage Va.

FIG. 10 is a diagram representing the relationship between ion current (arbitrary unit) and the ratio of DC voltage Vd to AC voltage Va. The DC voltage Vd and AC voltage Va can be freely set, but there is some restriction to ensure effective ionization. If the AC voltage has exceeded 100% of the DC voltage, the ionization efficiency will be reduced drastically. The present inventors have made experiments to find out the relationship between the ratio of DC voltage Vd to AC voltage Va and ion current to be generated. Assuming that the rate of the solution supplied to the ESI is 10 μL/min and DC voltage Vd is 2 kV, the AC voltage Va is changed to get the ion current value.

As shown in FIG. 10, when the AC voltage Va is 30% of the DC voltage Vd, the ion current value is the maximum. If it is 10% or less, the ion current value exhibits a sudden decline. If it is it 0%, namely, if there is no more alternating current, the ion current value will be reduced to about one third of the maximum value. If the alternating current has exceeded 30% of the direct current, ion current value starts a gradual decrease. If the alternating current is 100% of the direct current, the ion current value will be reduced to the same level as when no alternating current is applied. The preferred percentage is 10 to 65%, and more preferred one is 15 to 50%.

Figure 11:
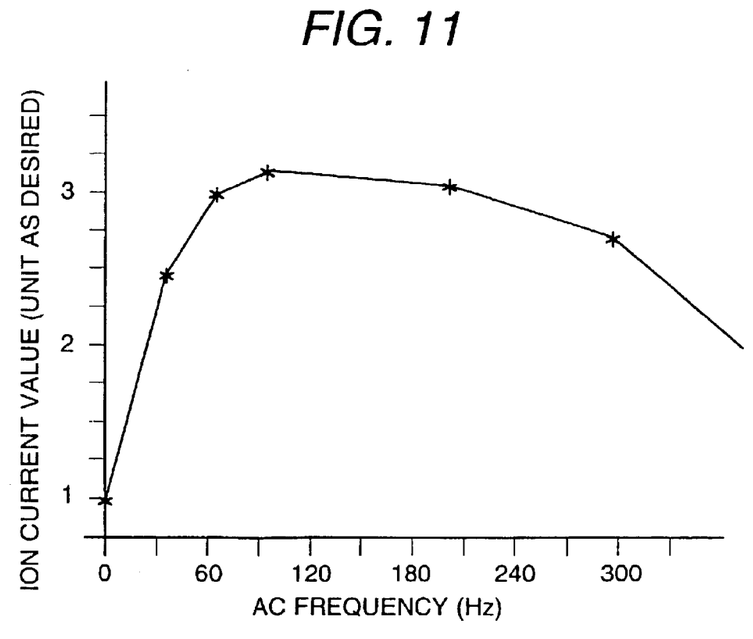
FIG. 11 is a diagram representing the relationship of the ion current (unit as desired) and AV voltage with respect to frequency.

FIG. 11 is a diagram representing the relationship of the ion current (arbitrary unit) and AV voltage with respect to frequency. As shown in FIG. 11, the frequency of the AC voltage Va to be applied affects the ion current value. The AC frequency has been increased from 10 Hz to 1 kHz to measure the ion current value. The ion current value increases to reach the maximum value at 80 to 100 Hz. Almost the flat ion current value is obtained up to 100 to 300 Hz. If frequency exceeds. 300 Hz, the ion current value exhibits a sudden decline. At 1 kHz, the ion current value is reduced to about one tenth of the level at 100 Hz. An acceptable cycle of the AC voltage is 1 kHz, and a preferable one is from 31 to 330 Hz. More preferably, it should be within the range from 50 to 300 Hz.

If a sufficiently longer time is assigned to the ion introduction and storage period than the cycle of the AC component of the applied voltage (HV), the AC modulation of the ion current value will be averaged out. Stable chromatogram and mass spectrum can be obtained if reproducibility is ensured despite any modulation. The applied alternating current is not restricted to sinusoidal waveform alone; it can be a rectangular or sawtooth waveform. The essential point is that reproducible stress is given to the tip of the Taylor Cone at all times. This will cause a fine vibration to the Taylor Cone itself. This fine vibration promotes discharge of charged minute droplet from the tip of the Taylor Cone.

In the Ionization which becomes unstable at a flow rate exceeding 1 μL/min in the normal ESI, this make it possible to receive the solution at a maximum rate of 100 μL/min from the ESI of the present invention, and satisfactory ionization can be achieved. Thus, the present invention ensures a stable and highly sensitive ionization to be carried out at a flow rate within the range from several tens of 10 μL/min to 1 μL/min.

INDUSTRIAL FIELD OF APPLICATION

The present invention provides an electrospray ionization ion trap mass analysis apparatus and its method that ensures the optimum sensitivity and stability in the flow rate range of micro liquid chromatograph.

What is claimed:

1. An electrospray ionization mass analysis apparatus characterized in that:

a sample solution is led into a minute capillary tube;

high voltage is applied to the tip of said capillary tube, thereby allowing a spray ion flow of said solution to be generated by an electrospray ion source provided therein; and the ion flow generated by said ion source is led to an ion storage type mass spectrometer disposed in a vacuum chamber where it is subjected to mass sweeping, and the swept ion is detected by a detector so that a mass spectrum is obtained;

said electrospray ionization mass analysis apparatus further characterized by comprising a high voltage DC power source for application of said high voltage formed by AC voltage superimposed on the DC voltage, and an AC power source.

2. An electrospray ionization mass analysis apparatus characterized in that:

a sample solution is separated by a micro liquid chromatograph;

said sample solution separated by said micro liquid chromatograph is led into a minute capillary tube;

high voltage is applied by a high voltage power source connected between the tip of the capillary tube and a counter electrode having an aperture, thereby allowing a spray ion flow to be generated to flow from the tip of the capillary tube toward the aperture by an electrospray ion source provided therein; and said ion flow generated by said ion source is sequentially led from the aperture to a skimmer cone and ion guide disposed in a vacuum chamber, then to the ion storage type mass spectrometer where it is subjected to mass sweeping, and the swept ion is detected by a detector so that a mass spectrum is obtained;

said electrospray ionization mass analysis apparatus further characterized in that said high voltage power source comprises a high voltage DC power source for application of DC voltage and an AC power supply for application of AC voltage, wherein the voltage is formed by said AC voltage superimposed on said DC voltage.

3. An electrospray ionization mass analysis apparatus according to claim 2 characterized in that said skimmer cone, ion guide and ion storage type mass spectrometer are each disposed integrally in each vacuum chamber, which is provided with a vacuum pump.

4. An electrospray ionization mass analysis apparatus according to claim 1 or 3 characterized in that an XYZ 3 axis positioner for setting the spray ion flow with respect to said capillary tube is connected.

5. An electrospray ionization mass analysis apparatus according to claim 4 characterized in that the ion storage type mass spectrometer is an ion trap mass spectrometer.

6. An electrospray ionization mass analysis apparatus according to claim 4 characterized in that the ion storage type mass spectrometer is an ion cyclotron resonance (ICR) mass spectrometer.

7. An electrospray ionization mass analysis apparatus characterized in that:

a sample solution is led into a minute capillary tube under atmospheric pressure;

high voltage is applied to the tip of said capillary tube, thereby allowing a spray ion flow of said solution to be generated; and the generated ion flow is led to an ion storage type spectrometer disposed in a vacuum chamber where it is subjected to mass sweeping, and the swept ion is detected by a detector so that a mass spectrum is obtained;

said electrospray ionization mass analysis apparatus further characterized in that the voltage formed by AC voltage superimposed on the DC voltage or the electric field formed by AC electric field superimposed on the static electric field is applied to the tip of said capillary tube.

8. An electrospray ionization mass analysis apparatus characterized in that:

a sample solution is separated by a micro liquid chromatograph;

the sample solution separated by the micro liquid chromatograph is led into a capillary tube;

high voltage is applied to the tip of the capillary tube, thereby allowing a spray ion flow to be generated to flow from the tip of the capillary tube; and the generated ion flow is sequentially led to a skimmer cone and ion guide disposed in a vacuum chamber, then to the ion storage type spectrometer where it is subjected to mass sweeping, and the swept ion is detected by a detector so that a mass spectrum is obtained;

said electrospray ionization mass analysis apparatus further characterized in that the voltage formed by AC voltage superimposed on the DC voltage or the electric field formed by AC electric field superimposed on the static electric field is applied to the tip of said capillary tube.

9. An electrospray ionization mass analysis apparatus according to claim 7 or 8 characterized in that said DC voltage and AC voltage or the intensity of static electric field and AC electric field can be set and controlled from the outside.

10. An electrospray ionization mass analysis apparatus according to claim 9 characterized in that, when said spray ion flow is in the positive ion measurement mode, the polarity of said DC voltage or static field is positive; and when said spray ion flow is in the negative ion measurement mode, the polarity of said DC voltage or static field is negative.

11. An electrospray ionization mass analysis apparatus according to claim 9 characterized in that said AC voltage is 100% or less of the DC voltage, or the AC electric field is 100% or less of the static electric field.

12. An electrospray ionization mass analysis apparatus according to claim 9 characterized in that the frequency of said AC voltage or AC electric field is 1 kHz or less.

13. An electrospray ionization mass analysis apparatus according to claim 9 characterized in that the flow rate of the solution led into the capillary tube is 50 $\mu$L/min or less.

14. An electrospray ionization mass analysis apparatus according to claim 9 characterized in that said storage type mass spectrometer is an ion trap type mass spectrometer, and the following four steps are incorporated:

(1) Preparatory step wherein the voltage formed by DC voltage superimposed on AC voltage is applied to the capillary tube, and voltage of the same polarity as that of ion is applied to the ion gate electrode arranged on the front stage of the ion trap type mass spectrometer so that the ion gate is turned off, followed by the process in which the main high frequency voltage applied to the ring electrode is reset to zero to remove all the ions in the ion trap;

(2) Ion introduction and storage step wherein voltage of the polarity reverse to that of ion is applied to the ion gate electrode so that the ion gate is turned on, and the main high frequency voltage is applied to the ring electrode so that the ion in a predetermined mass range is led into the ion trap, and ion storage is carried out for a predetermined period of time to level out the ion current;

(3) MS/MS step wherein voltage of the same polarity as that of ion is applied to the ion gate electrode so that the ion gate is turned off to block introduction of the ion, and the ion in said ion trap is selected to perform mass analysis mass spectrometry (MS/MS);

(4) Mass spectrum acquisition step wherein the main high frequency voltage applied to the ring voltage is swept and the ion in the ion trap is discharged out of the ion trap sequentially in the order of the mass, followed by the process of the ion current value being detected by a detector and the detected signal being fed to a control data processor, where a mass spectrum is obtained.

15. An electrospray ionization mass analysis apparatus according to claim 9 characterized in that high voltage applied to the tip of the capillary tube is set in such a way that the sample solution is formed in a Taylor cone shape at the outlet of the capillary tube.

* * * * *

UNITED STATES PATENT AND TRADEMARK OFFICE
CERTIFICATE OF CORRECTION

| | |
|---|---|
| PATENT NO. | : 6,737,640 B2 |
| DATED | : May 18, 2004 |
| INVENTOR(S) | : Yoshiaki Kato |

Page 1 of 1

It is certified that error appears in the above-identified patent and that said Letters Patent is hereby corrected as shown below:

<u>Title page,</u>
Item [87], PCT Filed date: "Mar. 31, 2002" should read -- Jan. 31, 2002 --.

Signed and Sealed this

Sixteenth Day of November, 2004

JON W. DUDAS
*Director of the United States Patent and Trademark Office*